US009006667B2

(12) United States Patent
Boday et al.

(10) Patent No.: US 9,006,667 B2
(45) Date of Patent: Apr. 14, 2015

(54) SURFACE-MODIFIED FLUORESCENT CARBON NANOTUBES FOR PRODUCT VERIFICATION

(75) Inventors: Dylan J. Boday, Tucson, AZ (US); Jason T. Wertz, Wappingers Falls, NY (US)

(73) Assignee: International Business Machines Corporation, Armonk, NY (US)

( * ) Notice: Subject to any disclaimer, the term of this patent is extended or adjusted under 35 U.S.C. 154(b) by 302 days.

(21) Appl. No.: 13/435,526

(22) Filed: Mar. 30, 2012

(65) Prior Publication Data
US 2013/0256529 A1 Oct. 3, 2013

(51) Int. Cl.
*G01J 1/58* (2006.01)
*G01N 33/58* (2006.01)
*C09K 11/02* (2006.01)

(52) U.S. Cl.
CPC .............. *G01N 33/587* (2013.01); *C09K 11/02* (2013.01); *G01N 33/582* (2013.01); *Y10S 977/742* (2013.01); *Y10S 977/745* (2013.01); *Y10S 977/75* (2013.01); *Y10S 977/752* (2013.01)

(58) Field of Classification Search
CPC .... C09K 11/02; C09K 11/0295; C09K 11/06; B82Y 25/10; G07D 7/122; G01N 33/587
USPC ................... 162/2; 427/7; 358/3.28; 283/72; 250/367, 483.1, 484.2, 458.1, 486.1; 977/742, 745, 750, 752
See application file for complete search history.

(56) References Cited

U.S. PATENT DOCUMENTS

| | | | |
|---|---|---|---|
| 4,558,224 A | 12/1985 | Gober | |
| 7,682,523 B2 | 3/2010 | Weisman et al. | |
| 7,879,575 B2* | 2/2011 | Kricka et al. | ...................... 435/8 |
| 7,976,609 B2 | 7/2011 | Niidome et al. | |
| 2004/0171175 A1* | 9/2004 | Swanson et al. | .............. 436/518 |

(Continued)

FOREIGN PATENT DOCUMENTS

| | | |
|---|---|---|
| JP | 11283276 A | 10/1999 |
| WO | 2009140266 A2 | 11/2009 |
| WO | 2011136521 A2 | 3/2011 |

OTHER PUBLICATIONS

Meng et al., "Advanced technology for functionalization of carbon nanotubes," Progress in Natural Science 19, (2009) 801-810.*

(Continued)

*Primary Examiner* — Yara B Green
(74) *Attorney, Agent, or Firm* — Jonathan V. Sry; Robert R. Williams (57) ABSTRACT

A material may include a medium and carbon nanotubes dispersed in the medium. Fluorescent moieties may be attached to functional groups on a first quantity of the carbon nanotubes. The fluorescent moieties may be in a concentration in the material sufficient to make the material fluoresce in the presence of radiation. The fluorescent moieties may have an emission wavelength that is in or below the visible spectrum. The carbon nanotubes may be dispersed in the medium in a concentration sufficient to make the material electrically conductive at or above the material's electrical percolation threshold. Any suitable product may include the material. Methods for verifying the authenticity of the product may include detecting emissive radiation, testing electrical conductivity, and determining the presence of a structural characteristic of the carbon nanotubes.

20 Claims, 6 Drawing Sheets

(56) References Cited

U.S. PATENT DOCUMENTS

| | | | |
|---|---|---|---|
| 2005/0008858 A1 | 1/2005 | Wakefield et al. | |
| 2007/0062411 A1 | 3/2007 | Weisman et al. | |
| 2008/0044651 A1 | 2/2008 | Douglas | |
| 2009/0280157 A1* | 11/2009 | Maas et al. | 424/426 |
| 2010/0038597 A1* | 2/2010 | Reynolds et al. | 252/500 |
| 2010/0209632 A1 | 8/2010 | Weisman et al. | |
| 2013/0098992 A1* | 4/2013 | Jenrick et al. | 235/375 |
| 2013/0230703 A1* | 9/2013 | Abrams et al. | 428/195.1 |

OTHER PUBLICATIONS

Tchoul et al., "Composites of Single-Walled Carbon Nanotubes and Polystyrene: Preparation and Electrical Conductivity," Chem. Mater. 2008, 20, 3120-3126.*

Blythe et al., "Electrical Properties of Polymers," Second Edition, Cambridge University Press, 2005.*

Han et al., "Functionalization of carbon nanotubes and other nanocarbons by azide chemistry," Nano-Micro Lett. vol. 2, p. 213-226 (2010); Retrieved from internet [Sep. 11, 2014]; Retrieved from <doi.10.5101.nml.v2i3.p213-226>.*

Kalinina et al., "Synthesis, Dispersion, and Viscosity of Poly(ethylene glycol)-Functionalized Water Soluble Single-Walled Carbon Nanotubes," Chemistry of Materials, vol. 23, p. 1246-1253 (Jan. 27, 2011); Retrieved from internet [Sep. 11, 2014]; Retrieved from url <http://pubs.acs.org/doi/pdf/10.1021/cm103030s>.*

Medintz et al., "Quantum dot bioconjugates for imaging, labelling, and sensing," Nature Materials, vol. 4, p. 435-446, (Jun. 2005); Retrieved from internet [Sep. 11, 2014]; Retrieved from url <www.nature.com/nmat/journal/v4/n6/nmat1390.html>.*

Pan et al., "Covalent attachemtn of quantum dots on carbon nanotubes," Chemical Physics Letters, vol. 417, p. 419-424 (Nov. 2005); Retrieved from internet [Sep. 12, 2014]; Retrieved from url <http:www.sciencedirect.com>.*

Kolmakov et al., "Red-Emitting Rhodamine Dyes for Fluorescence Microscopy and Nanoscopy," Chem. Eur. J., vol. 16, pp. 158-166 (2010); Retrieved from internet [Sep. 11, 2014]; Retrieved from url <http://dx.doi.org/10.1002/chem.200902309>.*

Nastase et al., "Nanocomposites based on functionalized nanotubes in polyaniline matrix by plasma polymerization," Progress in Solid State Chemistry, vol. 34, pp. 181-189 (2006); Retrieved from internet [Sep. 12, 2012]; Retrieved from url <http:www.sciencedirect.com>.*

Shi et al., "Quantum-Dot-Activated Luminescent Carbon Nanotubes via a Nano Scale Surface Functionalization for in vivo Imaging", Advanced Materials, Nov. 2007, pp. 4033-4037, vol. 19, Issue 22, Article first published online: Oct. 31, 2007, Copyright 2007 Wiley-VCH Verlag GmbH & Co. KGaA, Weinheim, Germany. DOI: 10.1002/adma.200700035.

* cited by examiner

SURFACE-MODIFIED FLUORESCENT CARBON NANOTUBES FOR PRODUCT VERIFICATION

TECHNICAL FIELD

This disclosure is generally directed to fluorescent surface-modified carbon nanotubes, and methods for producing and using the nanotubes. One such usage may be for the verification of the authenticity of a product or the purchasing of such product.

BACKGROUND

Carbon nanotubes are cylindrical nanostructures containing carbon atoms in a hexagonal arrangement primarily through $sp^2$ bonds. They can be created by a number of techniques, including chemical vapor deposition, arc discharge, and laser ablation. Carbon nanotubes have generally inert surfaces.

SUMMARY

One embodiment is directed to a material. The material may include a medium and carbon nanotubes may be dispersed in the medium. First fluorescent moieties may be attached to functional groups on a first quantity of the carbon nanotubes. The first fluorescent moieties may be in a concentration in the material sufficient to make the material fluoresce in the presence of radiation. In addition, in one embodiment, the carbon nanotubes may be dispersed in a concentration sufficient to make the material electrically conductive at or above the material's electrical percolation threshold.

Another embodiment is directed to a method for producing a material. The method may include providing a medium and dispersing carbon nanotubes in the medium. The method may include attaching first fluorescent moieties to functional groups on a first quantity of the carbon nanotubes. The first fluorescent moieties may be in a concentration in the material sufficient to make the material fluoresce in the presence of radiation. In addition, in one embodiment, the carbon nanotubes may be dispersed in a concentration sufficient to make the material electrically conductive at or above the material's electrical percolation threshold In addition, an embodiment is directed to a method for verifying the authenticity of a product having a material. The method may include exposing the material to incident radiation and detecting emissive radiation having a first emission wavelength to verify the authenticity of the product. The material may include a medium and carbon nanotubes dispersed in the medium. First fluorescent moieties may be attached to functional groups on a first quantity of the carbon nanotubes in a concentration sufficient to make the material fluoresce at the first emission wavelength in the presence of radiation. In one embodiment, the first emission wavelength is in or below the visible spectrum.

A further embodiment is directed to a method for verifying the authenticity of a product having a material. The method may include detecting emissive radiation having the second emission wavelength to verify the authenticity of the product. The material further may include second fluorescent moieties attached to functional groups on a second quantity of the carbon nanotubes in a concentration sufficient to make the material fluoresce at a second emission wavelength in the presence of radiation. The second fluorescent moieties may fluoresce at a second emission wavelength in or below the visible spectrum. The first and second emission wavelengths may be different wavelengths.

One embodiment is directed to detecting if the material fluoresces at a first predetermined intensity to verify the authenticity of the product.

Yet another embodiment is directed to a method for verifying the authenticity of a product having a material. The method may include testing the electrical conductivity of the material to verify the authenticity of the product. The material may include carbon nanotubes dispersed in a medium in a concentration sufficient to make the material electrically conductive at or above the material's electrical percolation threshold.

Moreover, an embodiment is directed to a method for verifying the authenticity of a product having a material. The material may include a medium and carbon nanotubes dispersed in the medium. The method may include inspecting the material using electron microscopy to determine the presence of a structural characteristic of the carbon nanotubes to verify the authenticity of the product.

BRIEF DESCRIPTION OF THE DRAWINGS

The drawings illustrate embodiments of the present invention and, along with the description, serve to explain the principles of the invention. The drawings are only illustrative of typical embodiments of the invention and do not limit the invention.

DETAILED DESCRIPTION

According to embodiments, the invention relates to a material which includes a carbon nanotube with a fluorescent moiety attached to the surface of the carbon nanotube. A carbon nanotube is functionalized and a fluorescent moiety is attached at a resulting functional group. A carbon nanotube may also be surface modified with a functional group or residual functionality for attaching the dye, which may aid in dispersion of the nanotube.

Fluorescent dyes may be used to mark or tag materials for fluorescent imaging. Due to their ability to emit light of a different wavelength from that which they absorb, fluorescent dyes can be used to create identifying marks that may not be apparent under ordinary lighting conditions. By imbuing an item with a fluorescent dye, a manufacturer creates an obstacle to counterfeiting due to the difficulty of both detecting the fluorescent mark and reproducing the mark. There are many applications for fluorescent dyes, including currency, identification cards, and correspondence documents.

Carbon Nanotube Functionalization

Carbon nanotubes are cylindrical nanostructures containing carbon atoms in a hexagonal arrangement primarily through $sp^2$ bonds. They can be created by a number of techniques, including chemical vapor deposition, arc discharge, and laser ablation. Carbon nanotubes have generally inert surfaces.

Due to the inert nature of carbon nanotubes, it is difficult to attach a moiety to a carbon nanotube wall without first making the carbon nanotube conducive to bonding. To facilitate attachment of a fluorescent moiety, the carbon nanotube may be first functionalized with a more reactive group, such as a carboxyl or hydroxyl group, after which one or more fluorescent moieties or other functional groups, such as ethylene glycol, may be attached to allow for further surface modifications.

Figure 1:
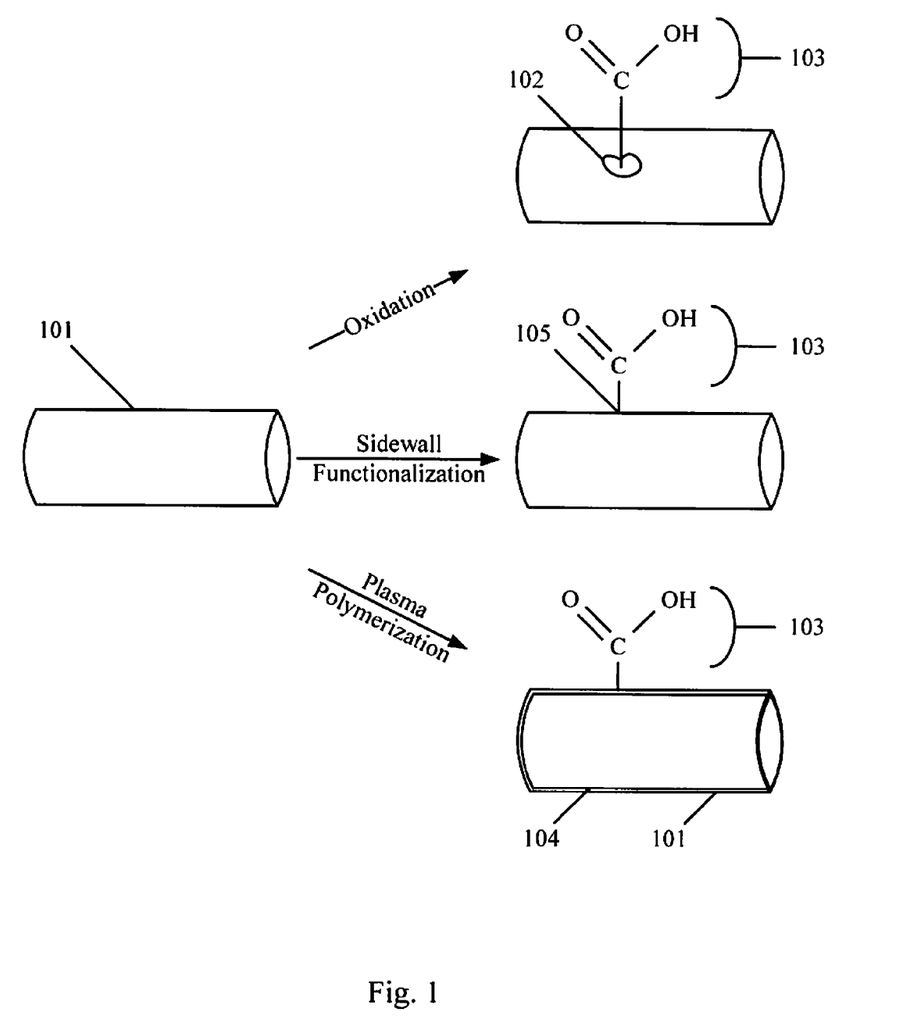
FIG. 1 depicts three possible processes for functionalizing the surface of a carbon nanotube, according to aspects of the invention.

There are a number of ways in which a carbon nanotube may be functionalized. In one embodiment, the carbon nanotube walls may be chemically functionalized through oxidation. Carbon nanotubes may be treated with an oxidizing agent, such as nitric acid or sulfuric acid, in varying strengths and durations, depending on the extent of oxidation desired. The bonds of the carbon nanotubes at their ends and at wall defects may be highly stressed, and may be more easily oxidized by the oxidizing agent than ordinary lateral carbon bonds of the walls. Under higher concentrations, the oxidizing agent may also break some of the ordinary lateral bonds of walls of the carbon nanotubes during oxidation. Oxidation creates functional groups on the oxidized wall surfaces, to which fluorescent moieties can be attached. These functional groups may include, but are not limited to, carboxyl, carbonyl, hydroxyl, and ester groups. The reaction, in this example producing a carboxyl group, may be as follows:

In another embodiment, the carbon nanotubes may be directly functionalized through sidewall functionalization. Carbon bonds of the nanotubes may be hybridized from $sp^2$ bonds to $sp^a$ bonds, and newly available bonds may attach to a functional group by addition reaction. The carbon nanotube sidewall remains intact, with functional groups coupled into the pi-conjugated surface of the carbon nanotubes. This functionalization may occur through fluorination, chlorination, radical attachment, or any other sidewall functionalization method. Any functional group may be added including, but not limited to, carboxyl, carbonyl, hydroxyl, and ester groups. For example, a functionalization reaction involving fluorination and formic acid may be as follows:

where a fluorine atom is attached to the carbon nanotube wall, and is subsequently replaced through nucleophilic substitution with a reactive functional group, in this case carboxyl.

In another embodiment, the carbon nanotube surface may be functionalized through the addition of a polymer film to the surface of the carbon nanotube, leaving the wall of the nanotube intact and the bonds unaffected. For example, in plasma polymerization, a radio-frequency source creates an electric field, which ionizes and activates a monomer containing pendant functional groups. The monomer polymerizes as a film on the wall of the carbon nanotube. This film contains the pendant functional groups, which can be used to bind to other molecules. These pendant functional groups may include, but are not limited to, carboxyl, carbonyl, hydroxyl, ester, amino, and nitro groups. The monomers may include, but are not limited to, acrylic acid and acetic acid.

FIG. 1 depicts three exemplary methods of functionalizing a carbon nanotube according to the present invention: oxidation, sidewall functionalization, and plasma polymerization. When a nanotube 101 undergoes oxidation, a carbon-carbon bond in the wall may break and one or more functional groups 103, in this example carboxyl, may form at a break 102. When a carbon nanotube 101 undergoes sidewall functionalization, an $sp^2$ carbon bond may hybridize to an $sp^3$ carbon bond 105, and one or more functional groups 103 may attach at the new bond site. When a carbon nanotube 101 undergoes plasma polymerization, a polymer film 104 may form over the carbon nanotube 101, and one or more functional groups 103 may form on the polymer film 104.

Fluorescent Moiety Attachment

After the carbon nanotubes are functionalized, fluorescent moieties may be added to the carbon nanotubes. Examples of fluorescent moieties include reactive fluorescent dyes and fluorescent quantum dots. In an embodiment of the invention, a reactive fluorescent dye is attached to a functional group on the surface of a carbon nanotube. A possible reaction, in this case using carboxyl as the functional group, is as follows:

According to embodiments, fluorescent moieties may be selected for their emission wavelengths from any region of the electromagnetic spectrum. Carbon nanotubes are naturally fluorescing, but typically only fluoresce in the infrared region (>750 nm). By attaching fluorescent moieties to the surfaces of the carbon nanotubes, the carbon nanotubes may fluoresce at a desired wavelength across the electromagnetic spectrum, according to the properties of the fluorescent moieties attached. Fluorescent moieties may be chosen from any suitable reactive fluorescent dye group that would bond with the functional group including, but not limited to, dansyl chloride, fluorescein, and rhodamine family compounds. In one embodiment, a fluorescent moiety has a wavelength of less than 750 nm. In one embodiment, a fluorescent moiety has an emission wavelength in or below the visible spectrum. A fluorescent moiety may be functionalized with a reactive group before attachment to the functionalized carbon nanotube to aid in bonding, such as through amidization or esterification.

In another embodiment, the fluorescent moieties are amine-functionalized quantum dots. Quantum dots are semi-conducting particles with characteristics defined by the size of the particles, of which fluorescence is one such characteristic. These dots may be more stable and less subject to leaching than reactive fluorescent moieties. A quantum dot typically contains a core made up of two or more metals forming a crystal lattice, and may contain a shell around the core. A quantum dot may have a functional group attached to the quantum dot that allows it to bind to another molecule, such as an amine or ester group. In this embodiment, the mechanism for attaching quantum dots to the carbon nanotube is the same as that used for attaching reactive fluorescent dyes. The quantum dots, however, are first amine-functionalized so that they are capable of attaching to the functional groups attached to the carbon nanotubes, as later described in the experimental protocol section. Quantum dot cores may be selected from any fluorescent quantum dot core material including, but not limited to, CdSe, CdTe, and GaN. Quantum dot shells, if desired, may include, but are not limited to, ZnS and CdSe. In one embodiment, an amine-functionalized quantum dot has an emission wavelength in or below the visible spectrum.

Figure 2:
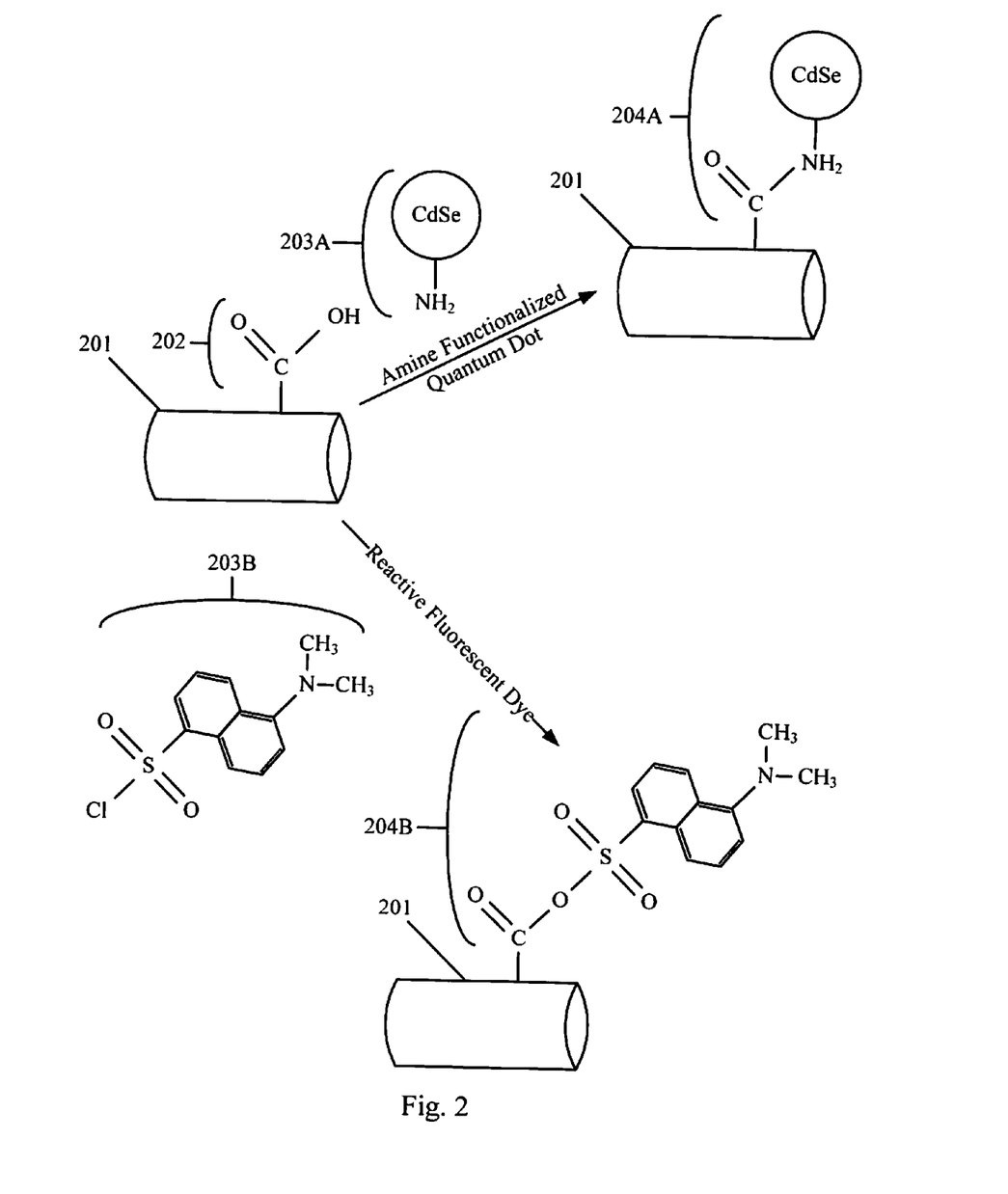
FIG. 2 depicts attachment of two exemplary fluorescent moieties to a functional group of a functionalized carbon nanotube, according to aspects of the invention.

FIG. 2 depicts fluorescent moiety attachment to the surface of a carbon nanotube 201, according to aspects of the invention. A functional group 202 is attached to the nanotube, in this example carboxyl. A fluorescent moiety 203A is shown, in this example an amine-functionalized quantum dot. The fluorescent moiety 203A and functional group 202 of the carbon nanotube undergo a coupling reaction; in this case, the hydroxyl of the carboxyl bonds with a hydrogen atom of the amine group, which is replaced with the nitrogen group of the quantum dot compound. A new fluorescent group 204A is bonded to the nanotube 201 forming a functionalized carbon nanotube. Alternately, a different fluorescent moiety 203B is shown, in this example dansyl chloride. The fluorescent moiety 203B and functional group 202 of the carbon nanotube undergo a coupling reaction; in this case, the chlorine atom of the dansyl chloride dissociates, and the sulfur atom displaces the hydrogen atom of the hydroxyl group of the carboxyl, bonding with the oxygen. A new fluorescent group 204B is bonded to the nanotube 201 forming a functionalized carbon nanotube. In an alternative embodiment, the carboxylic acid could be converted to a more conducive leaving group, such as acyl chloride, for attachment of a fluorescent moiety.

Functionalization of a carbon nanotube may lead to many functional groups on the walls of the carbon nanotube. In one embodiment, more than one fluorescent moiety may be attached to a carbon nanotube. In an embodiment, two or more fluorescent moieties are attached to a carbon nanotube in a material. The two or more fluorescent moieties attached to a carbon nanotube may be the same type of fluorescent moiety. Alternatively, the two or more fluorescent moieties attached to a carbon nanotube may be two or more different kinds of fluorescent moieties. In a process of making a material according to the principles of the invention, a plurality of types of fluorescent moieties may be added all at once during a moiety attachment stage, or in separate stages if desired. For example, both a rhodamine and a fluorescein dye, each having a different emission wavelength, may be attached to functional groups on a nanotube or group of nanotubes. In one embodiment, a fluorescent material may include first and second portions of carbon nanotubes. A first type of fluorescent moiety may be attached to the first portion of carbon nanotubes. A second type of fluorescent moiety may be attached to the second portion of carbon nanotubes. For example, rhodamine may be attached to the first portion of carbon nanotubes and a fluorescein dye may be attached to the second portion of carbon nanotubes. In an embodiment, attachment of more than one fluorescent moiety may be achieved by adjusting the reaction stoichiometry so that a first type of fluorescent moiety may not react with all the functional groups, leaving residual functional groups for attachment of a second type of fluorescent moiety.

The fluorescent moieties may be present on the carbon nanotubes in any concentration sufficient to allow the material to fluoresce at a desired intensity for an application. In one embodiment, a material according to the principles of the invention described herein may fluoresce at an intensity that may generally be observed without the aid of any equipment or machine. In one alternative, the material may fluoresce at an intensity that may generally be observed with the aid of equipment or a machine. Further, a material according to the principles of the invention may fluoresce at an emission wavelength below the visible spectrum, requiring the use of equipment or a machine to detect fluorescence.

Surface Modification for Dispersion

Carbon nanotubes are generally hydrophobic, and their properties may be changed in order to better disperse the nanotubes in aqueous or organic solvents, or to reduce agglomeration of the nanotubes. Functional groups formed during oxidation may aid in dispersion by polarizing the nanotube surfaces. In addition, functional groups formed during oxidation may reduce agglomeration by decreasing the van der Waals interactions between particles. Carboxylic acid is one example of a functional group that may be formed during oxidation. Nevertheless, dispersion characteristics greater than the dispersion characteristics provided by functionalization may be desired. In an embodiment, an additional modification may be made to carbon nanotubes having a fluorescent moiety according to the principles of the invention. The additional modification adds a dispersive functional group to carbon nanotubes to aid in dispersion into different media. The dispersive functional group may be hydrophilic functional groups or organic functional groups, depending on the characteristics of the medium used for dispersion. Dispersive functional groups may include, but are not limited to, ethylene glycol, octanol, and polyethylene glycol. This modification may occur before or after fluorescent moiety attachment. In one embodiment, the carbon nanotubes may be surface modified with a functional group to decrease agglomeration, such as an amine group. This may be done with any functional group that retards large-scale agglomeration including, but not limited to, carboxyl and amine groups.

Alternately, in addition to their fluorescent properties, the fluorescent moieties attached to the carbon nanotubes may be selected according to their ability to disperse in different media, eliminating the need to add a functional group to improve dispersion. In one embodiment, fluorescent moieties attached to carbon nanotubes may be hydrophilic or hydrophobic. In this embodiment, there may be no need to further functionalize the surfaces of the carbon nanotubes, as only the amount of fluorescent moieties may be varied to achieve dispersion.

Surface modification of the carbon nanotubes allows for dispersion of the carbon nanotubes in many different media. The carbon nanotubes may be dispersed in any suitable medium, including solvents and polymers. A suitable solvent may be polar or non-polar. The carbon nanotubes may be dispersed in a polar solvent including, but not limited to water, acetone, dimethylformamide, n-methyl-2-pyrrolidone, dichloroethylene, or chloroform. A surfactant may be used to disperse the carbon nanotubes in an aqueous solution including, but not limited to Triton X™, Triton X-100™, decylamine, dodecylamine, or hexadecylamine. The carbon nanotubes may be dispersed in a non-polar solvent including, but not limited to, acetates, alkanes, aromatics, and halogenated aromatic compounds. The carbon nanotubes may be dispersed in a polymer including, but not limited to, epoxies, latex, or polyurethanes.

Figure 3:
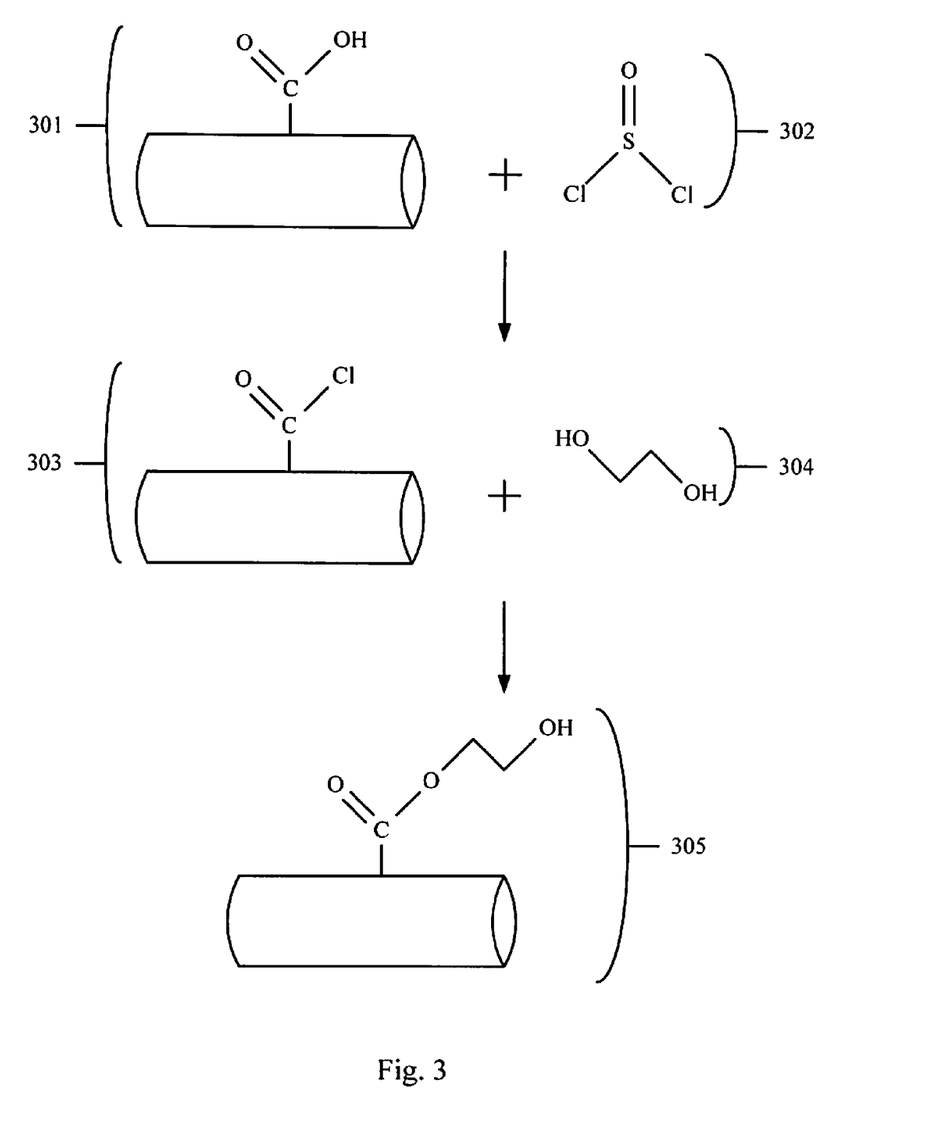
FIG. 3 depicts surface modification of carbon nanotubes with ethylene glycol for dispersion in a medium, according to aspects of the invention.

FIG. 3 depicts an embodiment of the surface modification of a carbon nanotube with a dispersive functional group, in this example for dispersion into an aqueous medium with an ethylene glycol functional group. A carboxylated carbon nanotube 301 is treated with a functional group 302, in this case thionyl chloride, to form a reactive functional group, in this case acyl chloride, on the carbon nanotube 303. This carbon nanotube 303 undergoes substitution with a dispersive functional group 304, in this case ethylene glycol, to form a surface modified carbon nanotube 305 having a dispersive property superior to a carbon nanotube without a dispersive functional group.

Electrical Conductivity

Figure 4:
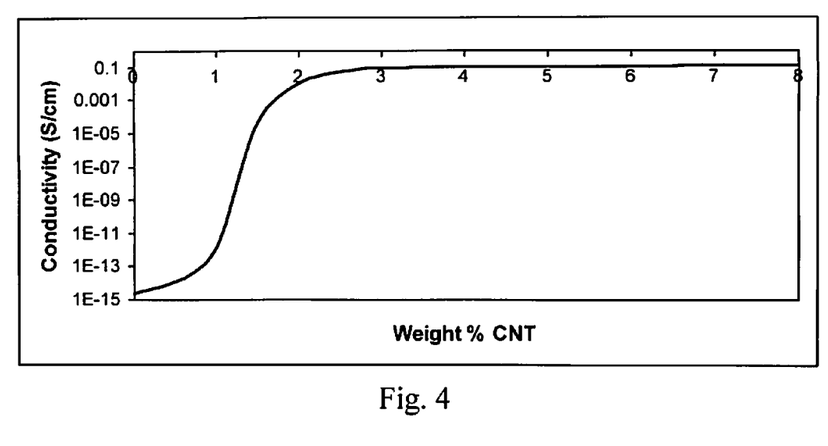
FIG. 4 depicts an exemplary relationship between material conductivity and nanotube concentration for a material, according to aspects of the invention.

Carbon nanotubes can exhibit electrical conductivity, and a material with a carbon nanotube concentration above that material's electrical percolation threshold may conduct electricity. Generally, when electrically conductive particles are dispersed into a medium, they form a material with a conducting network. The electrically conductive particles may be dispersed in a high enough concentration for the material to conduct electricity. This concentration is known as the electrical percolation threshold and is influenced by factors such as the medium in which the particles are dispersed, the temperature of the material, and the dispersion of the particles in the medium. Generally, as the weight fraction of the substance in the material or the temperature of the material increases, or as agglomeration of the particles decreases, the electrical percolation threshold decreases. The equation for conductivity near the percolation threshold is represented as follows:

$$\sigma = \sigma_c (\phi - \phi_c)^t$$

where $\sigma$ is the conductivity of the material, $\sigma_c$ is a conductivity constant of the material, $\phi$ is the weight fraction of electrically conductive particles in the material, $\phi_c$ is the percolation threshold of the material, and t is a scaling factor for the material. This equation may be used to determine the percolation threshold, as $\sigma_c$ and t for a material are known or may be determined experimentally. This equation only holds true near the percolation threshold, after which other effects such as tunneling come into consideration, though the material's conductivity will still increase as carbon nanotube concentration increases.

When carbon nanotubes are dispersed into a medium, the resulting material exhibits an electrical percolation threshold, as described above. In an embodiment, a material containing fluorescent surface-modified carbon nanotubes may be electrically conductive. As discussed above, the conductivity of the material will depend on the characteristics of the medium into which the nanotubes are dispersed and the concentration of nanotubes in the material. The graph in FIG. 4 depicts a curve illustrating a typical relationship between carbon nanotube concentration and material conductivity. While the shape of the curve shown in FIG. 4 is typical, the curve will vary based on the properties of the medium.

The percolation threshold is generally determined by plotting the log of material conductivity ($\sigma$) versus the log of the difference between the nanotube concentration and the percolation threshold ($\phi - \phi_c$). The resulting linear plot may be used to determine the material's conductivity constant ($\sigma_c$) and scaling factor (t), from which the percolation threshold ($\phi_c$) can be calculated. For a visual approximation, the percolation threshold can be seen in FIG. 4 as the sharp increase of conductivity with carbon nanotube concentration between 1 and 1½% (note that the y-axis of the graph is on a log scale). At carbon nanotube concentrations higher than the percolation threshold, the conductivity reaches a conductivity plateau, represented by a leveling out of conductivity with concentration, though this is not a true plateau, as the conductivity continues to increase with increasing nanotube concentration. A material with a carbon nanotube concentration at or above the percolation threshold will have a controllable and measurable resistivity. If, for example, a conductivity of 0.0001 S/cm is desired, the nanotube concentration may be 1.5%; if a conductivity of 0.01 S/cm is desired, the nanotube concentration may be 2%. Resistivity is inversely proportional to conductivity, and may be calculated so that resistivity can be measured in lieu of measuring conductivity. This characteristic of the invention may be discussed in either terminology without altering scope of the invention.

Product Verification and Anti-Counterfeit Security

A material according to the principles of the invention may be an ink or a paint that is applied or used to coat all or a portion of a surface of any product. In addition, a material according to the principles of the invention may be the substance used to make all or part of any product. Further, the material may be a constituent element of the substance used to make all or part of any product. For example, a product may include a part made from a substance that includes the material dispersed in that substance. Moreover, the material may be used in or on packaging for or a tag attached to any product.

A "product" may be any suitable product. Further, a product may be any packaging surrounding or attached to a product. A product may be any product used by business, government, or consumers. Examples of products include any integrated circuit and any circuit board having parts formed from or painted with a material having carbon nanotubes according to the principles of the invention. Other examples include consumer products, such as handbags, clothing, shoes, watches, jewelry, and electronic devices, such as cellular telephones having any part formed from a material containing carbon nanotubes according to the principles of the invention, or having a portion of an surface coated or painted with a material containing carbon nanotubes according to the principles of the invention. In one embodiment, a "product" may be a tag attached to a consumer product, such as an article of clothing, wherein the tag is formed from or painted with a material having carbon nanotubes according to the principles of the invention. An additional example of a product having a material formed from carbon nanotubes according to the principles of the invention may be packaging for any pharmaceutical product. For example, pharmaceuticals are commonly packaged in plastic bottles with labels affixed to the bottles. The plastic from which a bottle is made may include a material having carbon nanotubes as described herein or the label affixed to the bottle may have an ink printed thereon that includes a material having carbon nanotubes as described herein. As an additional example, a pharmaceutical product, such as a tablet or a capsule, may include a material having carbon nanotubes as described herein.

Figure 5:
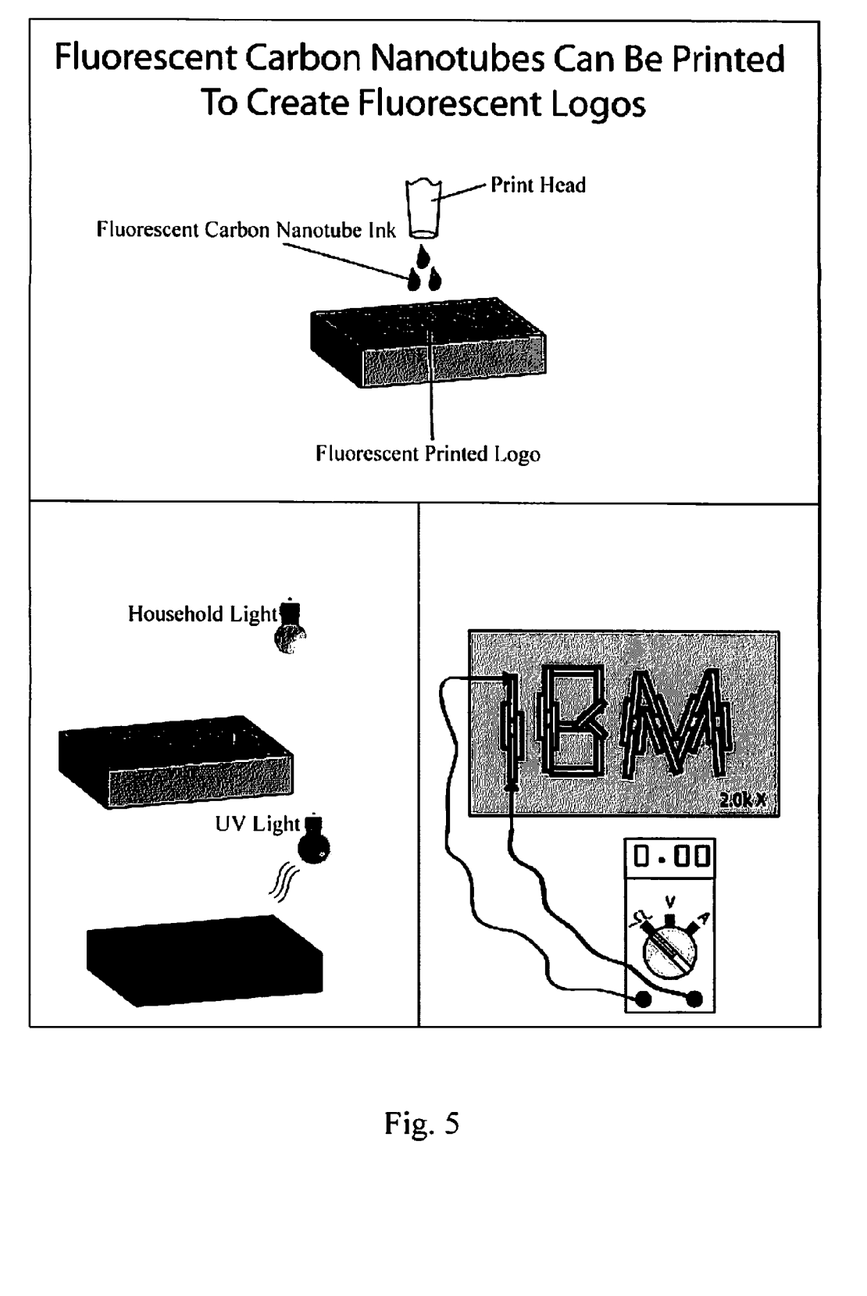
FIG. 5 depicts several possible applications of a fluorescent carbon nanotube ink in counterfeit security, according to aspects of the invention.

In one embodiment, a material may contain carbon nanotubes with one type of fluorescent moiety attached to the surface, which may be referred to as a first fluorescent moiety. The first fluorescent moiety may have an emission wavelength in or below the visible spectrum. For example, in one embodiment, the first fluorescent moiety may have an emission wavelength of less than 750 nm. In an alternative embodiment, a material may contain carbon nanotubes with two or more fluorescent moieties attached to the surface, wherein the moieties have different emission wavelengths in or below the visible spectrum. For example, a first moiety may have an excitation wavelength around 350 nm and an emission wavelength around 400 nm, while a second moiety may have an excitation wavelength around 550 nm and an emission wavelength around 600 nm. The nanotubes may be surface modified with a polarizing functional group and dispersed into a polar application system, such as an aqueous paint. The paint may be applied to a product. In one embodiment, the product may be irradiated with radiation at a wavelength of 365 nm to check for fluorescence at 400 nm. In the alternative embodiment, the product may be irradiated with radiation of a wavelength of 365 nm to check for fluorescence at 400 nm, and another light at 565 nm to check for fluorescence at 600 nm. If fluorescence is verified for both light sources, then the product may be verified as authentic. If fluorescence isn't present at both wavelengths, the product may be indentified as counterfeit. A counterfeiter must know to check a product for fluorescence, and must also know to check at multiple wavelengths. FIG. 5 depicts an application for fluorescence of nanotubes for use in logos.

In another embodiment of the invention, carbon nanotubes may be dispersed in a material in a concentration and level of dispersion so as to make the material electrically conductive with a particular conductance or at a particular resistance. In one embodiment, the material may be an ink or paint. The dispersion of carbon nanotubes in a material in sufficient concentration to make the material electrically conductive may be in addition to or as alternative to other embodiments described in this description, e.g., the attachment of fluorescent moieties or inspection of carbon nanotube shape or size using electron microscopy. As discussed earlier, conductivity is dependent on the properties of the material and the concentration of carbon nanotubes within the material, and can be graphed, calculated, or tested with respect to concentration for determination of a predetermined resistance.

To determine if a product is authentic, a current may be applied to a material and a voltage measured. Alternatively, a voltage may be applied to the material and a current measured. The material may be applied to a product such as an ink, paint, or coating. The substance from which any part of the product is made may include the material. A specific portion of a product may be coated with the material. The coated portion of the product will have the particular conductance or resistance. In one alternative, a specific portion of a product may be made from the material. The specific portion of the product made from the material will have the particular conductance or resistance. The resistance of the coated or specific portion may be measured to determine the authenticity of the product. A counterfeiter may not be aware of this electrical property or may not be able to replicate it. FIG. 5 depicts an application for conductivity of carbon nanotubes for use in logos.

In another embodiment, the authenticity of a product may be determined by examining the product using alternative microscopic techniques, such as electron microscopy. Material having carbon nanotubes according to the principles of the invention may be applied to a product as an ink, paint, or coating. Moreover, the substance from which any part of the product is made may include the material having carbon nanotubes according to the principles of the invention. The region of the product where the material is painted or coated may be examined with an electron microscope. Similarly, a part of the product that is made from a substance that includes the material may be examined with an electron microscope. Inspection with an electron microscope allows a structural characteristic such as the size or shape of the carbon nanotubes to be examined. For example, the process of forming or cutting the nanotubes may be controlled in order to create nanotubes of a certain homogeneous size or shape, such as through chemical vapor deposition. To test for product authenticity, the size or shape of the carbon nanotubes in a material may be inspected and compared with the "controlled for" size or shape of the carbon nanotubes. For particularly expensive or unique products, a counterfeiter may determine the proper emission wavelengths for the fluorescent moieties and the predetermined electrical resistance for the nanotubes, and apply them to the counterfeit product, but might not properly determine the size or physical structure of the nanotubes. The inspection of carbon nanotube shape or size using electron microscopy may be in addition to or as alternative to other embodiments described in this description, e.g., the attachment of fluorescent moieties or the dispersion of carbon nanotubes in a material in sufficient concentration to make the material electrically conductive. FIG. 5 depicts an application for electron microscopy of nanotubes for use in insignia or logos.

These different levels of security can be tailored to an anti-counterfeit system according to the needs of the business and characteristics of the product. For selected items, based on the items' cost, importance, or other distinguishing factor, a system can be tailored to test for fluorescence at multiple wavelengths as well as test for electrical conductivity at specific resistances. But for more expensive or unique items, the electron microscope can be applied. The actual anti-counterfeiting medium need not change, only the systems used to check for counterfeiting, though characteristics of the material such as dilution can be changed to allow for customization.

Figure 6:
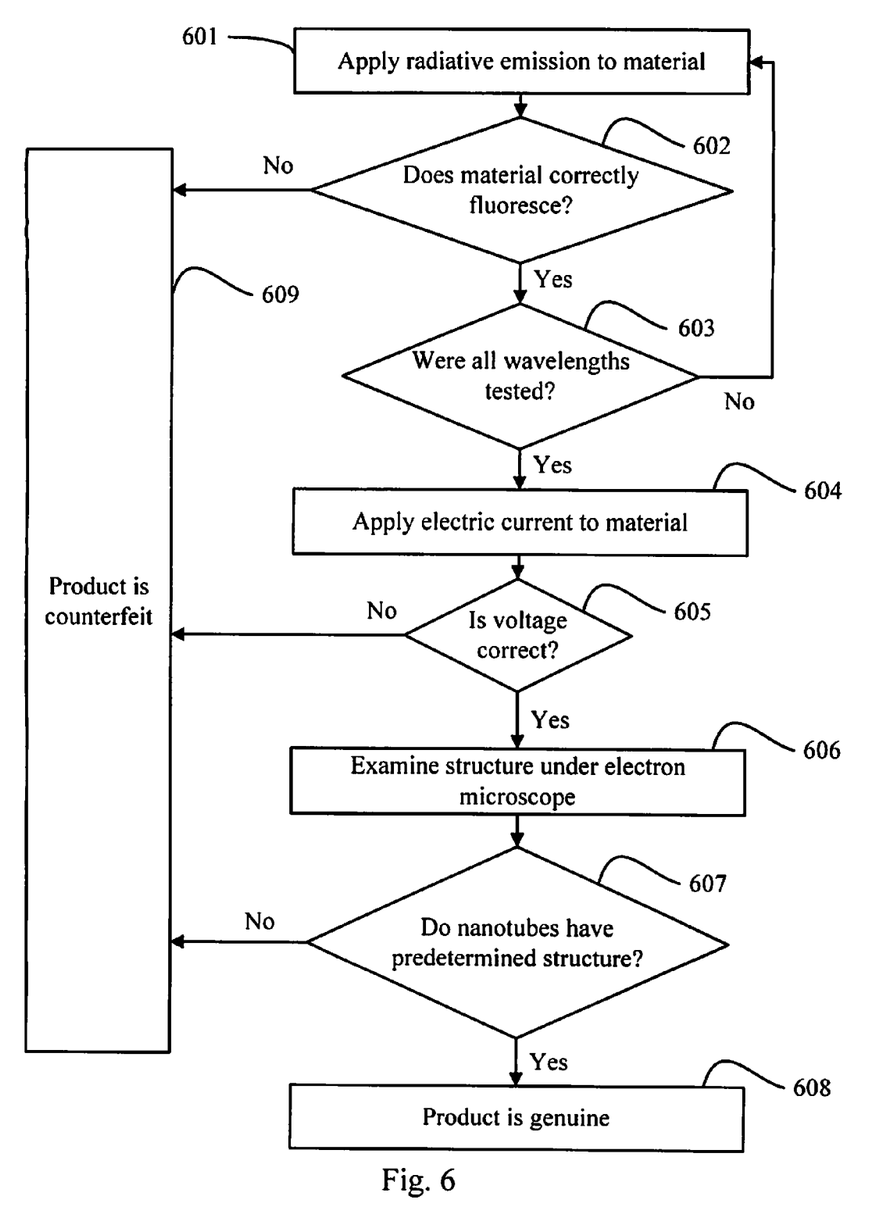
FIG. 6 depicts methods for using carbon nanotubes to verify product authenticity, according to aspects of the invention.

FIG. 6 depicts an exemplary method for determining whether a product is authentic according to embodiments of the invention. In 601, a product having a material according to the principles of the invention is exposed to incident radiation. In one embodiment, all or part of the material is exposed to incident radiation. In 602, fluorescence may be checked at a first predetermined wavelength; if the material does not fluoresce at the correct wavelength, then it may be determined that the product is not authentic, i.e., counterfeit, as in 609. On the other hand, if the material does fluoresce at the correct wavelength, it may be determined that the product is authentic. Alternatively, in operation 609, it may be determined if the material fluoresces at a first predetermined wavelength and if the material fluoresces at a first predetermined intensity. If the material does not fluoresce at the correct wavelength and intensity, then it may be determined that the product is not authentic. On the other hand, if the material does fluoresce at the correct wavelength and intensity, it may be determined that the product is authentic. The operation 602 may only include checking fluorescence at a first predetermined wavelength. Optionally, however, the operation 602 may include checking fluorescence at two or more predetermined wavelengths. In this embodiment, the test may be repeated until all wavelengths have been tested, as in 603. For example, the operation 602 may include checking fluorescence at first and second predetermined wavelengths. If the material fluoresces at the first and second predetermined wavelengths, it may be determined that the product is authentic. On the other hand, if the material does not fluoresce at both wavelengths, then it may be determined that the product is not authentic. In one embodiment, a method for determining whether a product is authentic may terminate with operation 603. Alternatively, one or more additional tests may be performed.

In one embodiment an additional test is performed in operation 604. In operation 604, an electric current may be applied to the material, and checked in 605 to determine whether an expected conductance or resistance is measured. If the measured conductance or resistance is not as expected, it may be determined that the product is not authentic, as in 609. If the measured conductance or resistance is as expected, then it may be determined that the product is authentic. Operations 604 and 605 may be performed alone to determine the authenticity of a product. Alternatively, the operations 604 and 605 may be performed together with another test described herein to determine the authenticity of a product. In one embodiment, a method for determining whether a product is authentic may terminate with operation 605. Alternatively, one or more additional test may be performed.

In one embodiment an additional test is performed in operation 606. In operation 606, the structure of the carbon nanotubes in the material may be examined using electron microscopy. Operation 606 may include inspecting the size or shape or other structural characteristic of the carbon nanotubes in a material and comparing an observation with an expected or "controlled for" size or shape of the carbon nanotubes. In operation 607, it may be determine if the observed structural characteristic is substantially the same as the expected structural characteristic. If the expected structure is not observed, then it may be determined that the article is not authentic, as in 609. If the expected structure is observed, then it may be determined that the product is genuine, as in 608.

Illustrative Experimental Protocols

The following illustrative experimental protocols are prophetic examples which may be practiced in a laboratory environment.

1. Preparation of Fluorescent Carbon Nanotubes—Plasma Polymerization, Quantum Dots Carbon nanotubes are treated with an acid solution consisting of nitric acid, sulfuric acid, and water to form Solution A. An acrylic acid solution is added to Solution A to form Solution B, and a radio-frequency is applied. CdSe/ZnS quantum dots (10 nmols/mL) are added to an ammonia/water solution to form Solution C, and kept between a 1:1 and 1:4 ratio with the nanotubes; Solution C is added to Solution B to form Solution D. 1-(3-dimethylaminopropyl)-3-ethylcarbodiimide hydrochloride and N-hydroxysuccinimide are present as stabilizers in a phosphate buffer saline solution (35 μmols/mL) to form Solution E with a pH of 7.4; Solution E is added to solution D. The resulting suspension is incubated for 8 hours at 42° C. After incubation, the suspension is cooled to room temperature, centrifuged for one hour, and rinsed in phosphate buffer saline solution.

2. Preparation of Dispersive Fluorescent Carbon Nanotubes—Acid Oxidation, Dansyl Chloride, Ethylene Glycol Surface Modification To a 100 mL round bottom flask, multiwall carbon nanotubes (80 nm dia. 1.0 g) are added along with a stir bar. To the round bottom flask, a solution containing nitric acid (30 mL), sulfuric acid (7.5 mL), and water (3 mL) is added. The round bottom flask is attached to a condenser and the reaction is heated to reflux for 96 hr. Carboxylic acid modified nanotubes are purified by centrifugation and the supernatant is decanted off the nanotube. The nanotubes are then redispersed in deionized water. This process is repeated until the pH of decanted solution is the same as the deionized water.

To a 100 mL round bottom flask, dried carboxylic acid multiwall carbon nanotubes (0.25 g.) are added along with a magnetic stir bar. To this round bottom flask, thionyl chloride (10 mL) is added and the round bottom flask is quickly attached to a condenser. The reaction is heated to reflux for 24 hr. The residual thionyl chloride is removed via distillation. The round bottom flask is back-filled with argon. To the acyl chloride modified carbon nanotubes, ethylene glycol (20 mL) is added and the reaction is heated to 120° C. for 48 hr. The glycol modified nanotubes are purified by centrifugation and the supernatant decanted off the nanotubes. The nanotubes are then redispersed in tetrahydrofuran. This process is repeated 3 times.

To a 100 mL round bottom flask, the glycol modified carbon nanotubes (0.5 g) are added along with triethyleamine (0.3 g) in anhydrous tetrahydrofuran. Then dansyl chloride (0.43 g) dissolved in tetrahydrofuran (10 mL) is added drop wise and magnetically stirred for 48 hr. The carbon nanotubes are purified by filtration. The carbon nanotubes are washed with tetrahydrofuran to remove excess dansyl chloride.

What is claimed is:

1. A material, comprising:
   a medium;
   carbon nanotubes dispersed in the medium;
   first fluorescent moieties attached to functional groups on a first quantity of the carbon nanotubes, the first fluorescent moieties being in a concentration in the material sufficient to make the material fluoresce in the presence of radiation, wherein the first fluorescent moieties fluoresce at a first emission wavelength in the visible spectrum, wherein attached means covalently bonded; and
   second fluorescent moieties attached to functional groups on the first quantity of the carbon nanotubes in a concentration sufficient to make the material fluoresce in the presence of radiation, wherein a first fluorescent moiety and a second fluorescent moiety are attached to functional groups on the same carbon nanotube from the first quantity of the carbon nanotubes,
   wherein the second fluorescent moieties fluoresce at a second emission wavelength in the visible spectrum, and the first and second emission wavelengths are different wavelengths.

2. The material of claim 1, wherein the carbon nanotubes are dispersed in a concentration sufficient to make the material electrically conductive at or above the material's electrical percolation threshold, wherein the medium is nonconductive.

3. The material of claim 1, wherein the first fluorescent moieties are hydrophobic.

4. The material of claim 1, further comprising a dispersive functional group attached to one or more of the carbon nanotubes, wherein the dispersive functional group is selected from ethylene glycol, octanol, and polyethylene glycol.

5. The material of claim 1, wherein the first fluorescent moieties is a rhodamine family compound.

6. The material of claim 1, wherein the functional group is a carboxyl-group.

7. The material of claim 1, wherein the first fluorescent moieties is an amine-functionalized quantum dot selected from a fluorescent quantum dot core material of CdSe, CdTe, and GaN.

8. The material of claim 1, wherein the first fluorescent moieties is dansyl chloride.

9. A method for producing a material, comprising:
   providing a medium;
   dispersing carbon nanotubes in the medium;
   attaching first fluorescent moieties to functional groups on a first quantity of the carbon nanotubes, the first fluorescent moieties being in a concentration in the material sufficient to make the material fluoresce in the presence of radiation, wherein the first fluorescent moieties fluoresce at a first emission wavelength in the visible spectrum, wherein attaching includes creating a covalent bond between the first fluorescent moieties and the functional groups on the first quantity of the carbon nanotubes; and
   attaching second fluorescent moieties to functional groups on the first quantity of the carbon nanotubes, the second fluorescent moieties being in a concentration in the material sufficient to make the material fluoresce in the presence of radiation, wherein a first fluorescent moiety and a second fluorescent moiety are attached to functional groups on the same carbon nanotube from the first quantity of the carbon nanotubes, wherein the second fluorescent moieties fluoresce at a second emission wavelength in the visible spectrum, and the first and second emission wavelengths are different wavelengths.

10. The method of claim 9, wherein the carbon nanotubes are dispersed in a concentration sufficient to make the material electrically conductive at or above the material's electrical percolation threshold, wherein the medium is nonconductive.

11. The method of claim 9, wherein the first fluorescent moieties are hydrophobic.

12. The method of claim 9, further comprising attaching a dispersive functional group to one or more of the carbon nanotubes, wherein the dispersive functional group is selected from ethylene glycol, octanol, and polyethylene glycol.

13. The method of claim 9, wherein the first fluorescent moieties are attached on the first quantity of the carbon nanotubes by at least one of: oxidation, sidewall functionalization, and plasma polymerization.

14. The method of claim 13, wherein the plasma polymerization includes:
 activating a monomer containing a pendant functional group; and
 polymerizing the monomer on a wall of the carbon nanotube.

15. The method of claim 9, wherein attaching first fluorescent moieties to functional groups on a first quantity of the carbon nanotubes includes:
 attaching an amine-functionalized quantum dot to the functional group, wherein the functional group on the first quantity of the carbon nanotubes is a carboxyl-group.

16. A method for verifying authenticity of a product having a material, comprising:
 exposing the material to incident radiation, the material including a medium and carbon nanotubes dispersed in the medium, wherein first fluorescent moieties are attached to functional groups on a first quantity of the carbon nanotubes in a concentration sufficient to make the material fluoresce at a first emission wavelength in the presence of radiation, wherein the carbon nanotubes with the first fluorescent moieties attached have a certain homogeneous size and shape;
 detecting emissive radiation having a first emission wavelength within the visible spectrum to verify the authenticity of the product;
 inspecting the material using electron microscopy to determine the certain homogeneous size and shape of the carbon nanotubes, and
 comparing the homogeneous size and shape of the carbon nanotube to a controlled for size and shape of the carbon nanotube to verify the authenticity of the product.

17. The method of claim 16, wherein the material further includes second fluorescent moieties attached to functional groups on the first quantity of the carbon nanotubes in a concentration sufficient to make the material fluoresce at a second emission wavelength in the presence of radiation, wherein a first fluorescent moiety and a second fluorescent moiety are attached to functional groups on the same carbon nanotube from the first quantity of the carbon nanotubes and wherein the second fluorescent moieties fluoresce at a second emission wavelength in the visible spectrum, and the first and second emission wavelengths are different wavelengths, further comprising:
 detecting emissive radiation having the second emission wavelength to verify the authenticity of the product.

18. The method of claim 16, further comprising:
 detecting, at the first emission wavelength, if the material fluoresces at a first predetermined intensity to verify the authenticity of the product.

19. The method of claim 16, wherein the carbon nanotubes are dispersed in the medium in a concentration sufficient to make the material electrically conductive at or above the material's electrical percolation threshold, wherein the medium is nonconductive.

20. The method of claim 19, further comprising testing the electrical conductivity of the material to verify the authenticity of the product.

\* \* \* \* \*